(12) United States Patent
Hathaway et al.

(10) Patent No.: US 8,579,921 B2
(45) Date of Patent: Nov. 12, 2013

(54) SPRING-TYPE SUTURE SECURING DEVICE

(75) Inventors: Peter Hathaway, Lebanon, CT (US);
Kevin Sniffin, Danbury, CT (US);
Matthew Chowaniec, Middletown, CT (US); Eric Taylor, East Hampton, CT (US)

(73) Assignee: Covidien LP, Mansfield, MA (US)

( * ) Notice: Subject to any disclaimer, the term of this patent is extended or adjusted under 35 U.S.C. 154(b) by 806 days.

(21) Appl. No.: 12/484,653

(22) Filed: Jun. 15, 2009

(65) Prior Publication Data

US 2009/0318938 A1   Dec. 24, 2009

Related U.S. Application Data

(60) Provisional application No. 61/073,470, filed on Jun. 18, 2008.

(51) Int. Cl.
*A61B 17/04* (2006.01)
(52) U.S. Cl.
USPC ............ 606/148; 606/139; 606/144; 606/205
(58) Field of Classification Search
USPC ............. 606/139, 144, 145, 148, 232, 1, 205, 606/206; 607/127, 131; 289/17
See application file for complete search history.

(56) References Cited

U.S. PATENT DOCUMENTS

| | | |
|---|---|---|
| 4,669,471 A | 6/1987 | Hayashi |
| 4,945,920 A | 8/1990 | Clossich |
| 4,950,273 A | 8/1990 | Briggs |
| 4,982,727 A | 1/1991 | Sato |
| 5,035,248 A | 7/1991 | Zinnecker |
| 5,080,663 A | 1/1992 | Mills et al. |
| 5,100,430 A | 3/1992 | Avellanet et al. |
| 5,133,727 A | 7/1992 | Bales et al. |
| 5,137,013 A | 8/1992 | Chiba et al. |
| 5,152,779 A | 10/1992 | Sanagi |
| 5,209,747 A | 5/1993 | Knoepfler |
| 5,228,451 A | 7/1993 | Bales et al. |
| 5,238,002 A | 8/1993 | Devlin et al. |
| 5,254,130 A | 10/1993 | Poncet et al. |
| 5,275,608 A | 1/1994 | Forman et al. |
| 5,308,353 A | 5/1994 | Beurrier |
| 5,318,528 A | 6/1994 | Heaven et al. |
| 5,330,502 A | 7/1994 | Hassler et al. |
| 5,336,221 A | 8/1994 | Anderson |
| 5,350,391 A | 9/1994 | Iacovelli |
| 5,354,311 A * | 10/1994 | Kambin et al. ............... 606/205 |
| 5,383,888 A | 1/1995 | Zvenyatsky et al. |
| 5,383,895 A | 1/1995 | Holmes et al. |
| 5,403,342 A | 4/1995 | Tovey et al. |
| 5,411,481 A | 5/1995 | Allen et al. |
| 5,417,203 A | 5/1995 | Tovey et al. |

(Continued)

*Primary Examiner* — Darwin Erezo
*Assistant Examiner* — Jing Ou

(57) ABSTRACT

A suture securing device includes a body with a distal end portion defining a suture receiving opening; a shaft and the body being assembled for relative reciprocal motion between a first position and a second position; and a tension coil spring operably attached to the body and operably attached adjacent a distal end portion of the shaft and disposed adjacent a suture receiving opening, When the body and shaft are in the first position, the tension coil spring is in a rest position, and when the body and/or the shaft are in the second position, the tension coil spring is in a tensioned position to form at least one gap therebetween to enable receipt of at least a portion of at least one suture.

12 Claims, 15 Drawing Sheets

(56) References Cited

U.S. PATENT DOCUMENTS

| | | |
|---|---|---|
| 5,419,339 A | 5/1995 | Palmer |
| 5,437,682 A * | 8/1995 | Grice et al. .................. 606/148 |
| 5,439,467 A | 8/1995 | Benderev et al. |
| 5,454,378 A | 10/1995 | Palmer et al. |
| 5,474,571 A | 12/1995 | Lang |
| 5,480,406 A | 1/1996 | Nolan et al. |
| 5,490,861 A | 2/1996 | Kratsch et al. |
| 5,514,157 A | 5/1996 | Nicholas et al. |
| 5,520,678 A | 5/1996 | Heckele et al. |
| 5,527,322 A | 6/1996 | Klein et al. |
| 5,535,754 A | 7/1996 | Doherty |
| 5,545,148 A | 8/1996 | Wurster |
| 5,549,617 A | 8/1996 | Green et al. |
| 5,562,686 A | 10/1996 | Sauer et al. |
| 5,569,269 A | 10/1996 | Hart et al. |
| 5,569,299 A | 10/1996 | Dill et al. |
| 5,571,119 A | 11/1996 | Atala |
| 5,571,136 A | 11/1996 | Weaver |
| 5,578,056 A | 11/1996 | Pauldrach |
| 5,582,617 A | 12/1996 | Klieman et al. |
| 5,591,202 A | 1/1997 | Slater et al. |
| 5,601,599 A | 2/1997 | Nunez |
| 5,607,450 A | 3/1997 | Zvenyatsky et al. |
| 5,643,294 A | 7/1997 | Tovey et al. |
| 5,674,230 A | 10/1997 | Tovey et al. |
| 5,692,668 A | 12/1997 | Schulze et al. |
| 5,702,408 A | 12/1997 | Wales et al. |
| 5,704,534 A | 1/1998 | Huitema et al. |
| 5,728,107 A | 3/1998 | Zlock et al. |
| 5,728,113 A | 3/1998 | Sherts |
| 5,766,205 A | 6/1998 | Zvenyatsky et al. |
| 5,792,152 A | 8/1998 | Klein et al. |
| 5,797,959 A | 8/1998 | Castro et al. |
| 5,830,220 A | 11/1998 | Wan et al. |
| 5,871,488 A | 2/1999 | Tovey et al. |
| 5,908,428 A | 6/1999 | Scirica et al. |
| 5,919,199 A | 7/1999 | Mers Kelly et al. |
| 5,957,903 A * | 9/1999 | Mirzaee et al. ................ 604/524 |
| 5,993,467 A | 11/1999 | Yoon |
| 6,022,360 A * | 2/2000 | Reimels et al. ................ 606/144 |
| 6,139,563 A | 10/2000 | Cosgrove, III et al. |
| 6,206,893 B1 | 3/2001 | Klein et al. |
| 6,554,845 B1 | 4/2003 | Fleenor et al. |
| 6,699,263 B2 * | 3/2004 | Cope ........................... 606/232 |
| 6,743,239 B1 | 6/2004 | Kuehn et al. |
| 6,991,627 B2 | 1/2006 | Madhani et al. |
| 6,997,931 B2 | 2/2006 | Sauer et al. |
| 7,087,071 B2 | 8/2006 | Nicholas et al. |
| 7,090,637 B2 | 8/2006 | Danitz et al. |
| 2003/0060774 A1 * | 3/2003 | Woehr et al. .................. 604/192 |
| 2003/0195562 A1 * | 10/2003 | Collier et al. ................. 606/232 |
| 2003/0233104 A1 | 12/2003 | Gellman et al. |
| 2005/0251112 A1 | 11/2005 | Danitz et al. |
| 2006/0004409 A1 * | 1/2006 | Nobis et al. .................. 606/232 |
| 2006/0004410 A1 * | 1/2006 | Nobis et al. .................. 606/232 |
| 2006/0095074 A1 * | 5/2006 | Lee et al. ...................... 606/205 |
| 2006/0195140 A1 * | 8/2006 | Banju et al. ................... 606/205 |
| 2007/0083235 A1 * | 4/2007 | Jervis et al. ................... 606/232 |
| 2007/0221701 A1 * | 9/2007 | Ortiz et al. .................. 227/175.1 |
| 2008/0262537 A1 * | 10/2008 | Lee et al. ...................... 606/205 |

* cited by examiner

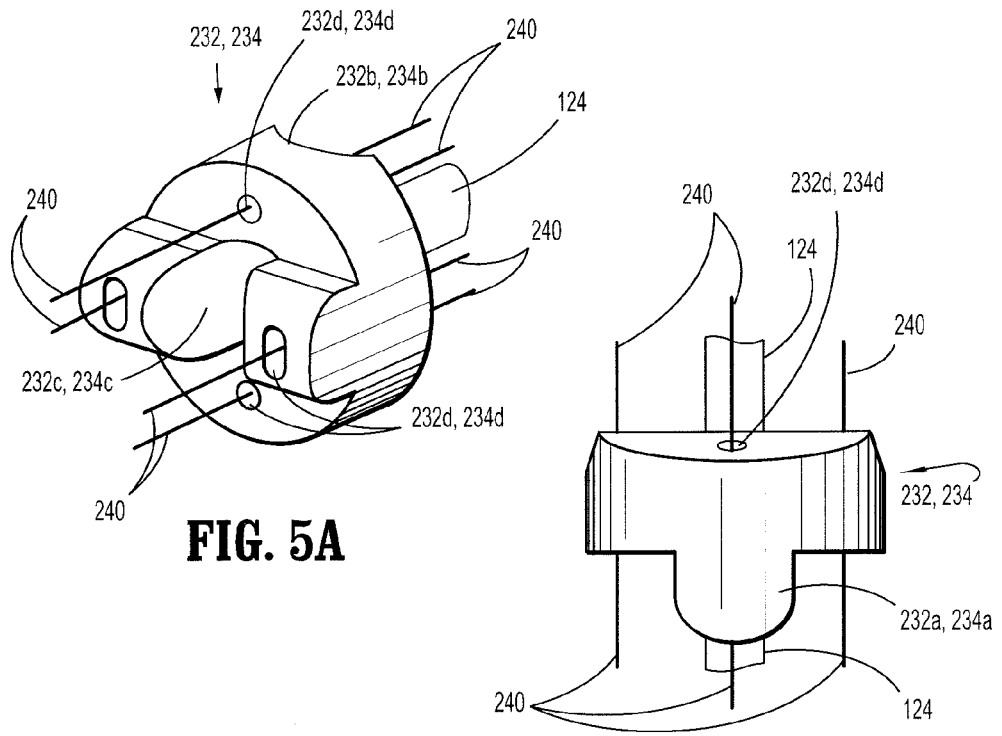
FIG. 5A
FIG. 5B
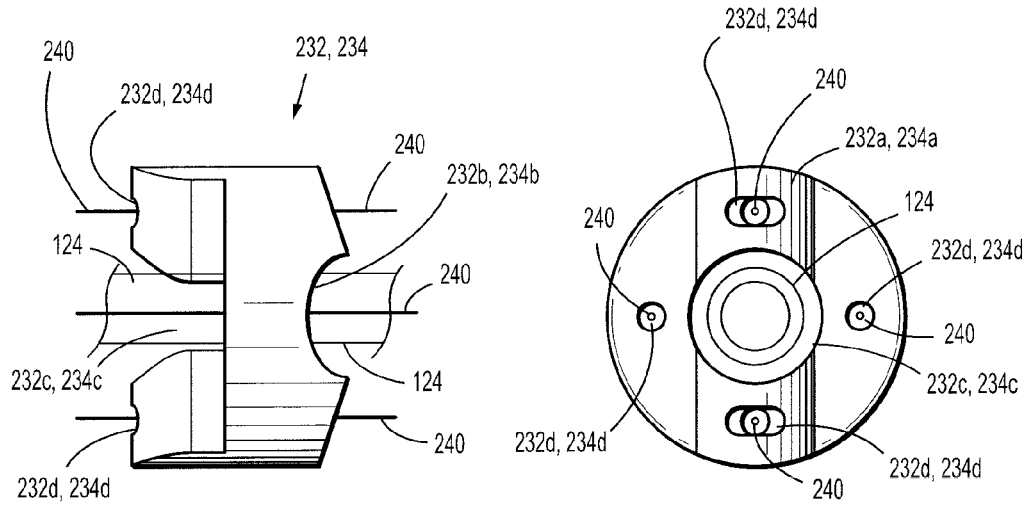
FIG. 5D
FIG. 5C

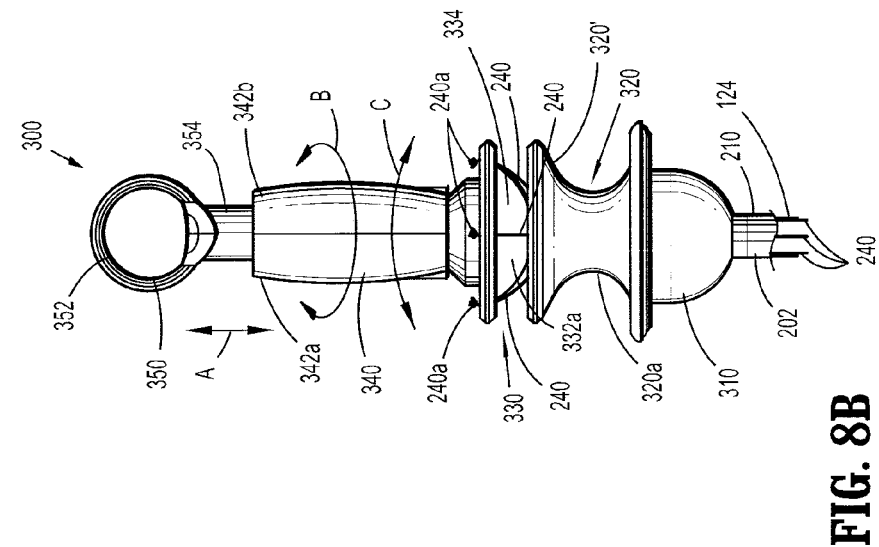
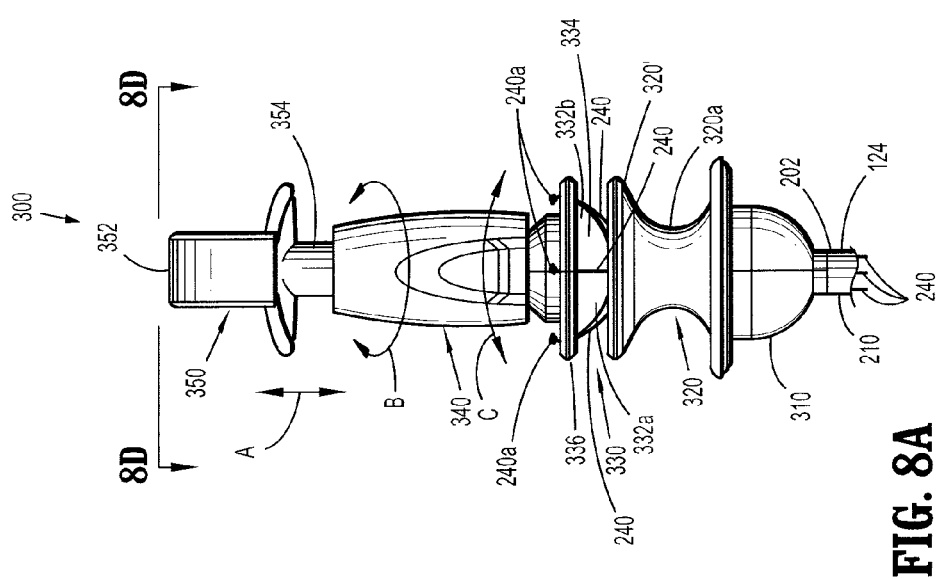
FIG. 8B
FIG. 8A

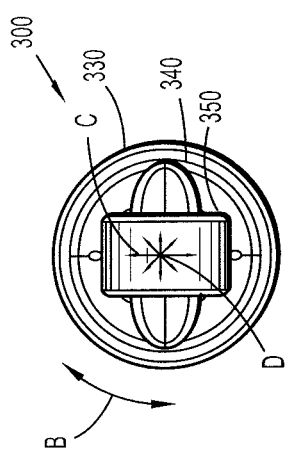
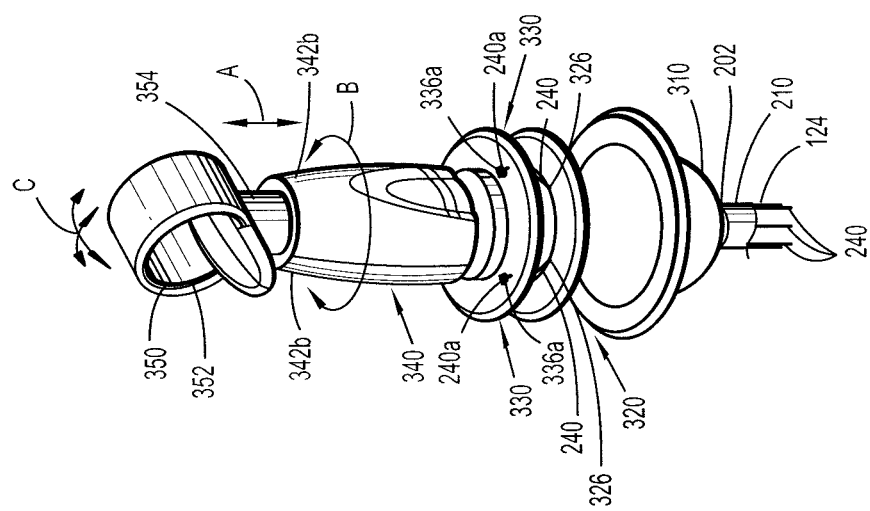

SPRING-TYPE SUTURE SECURING DEVICE

CROSS-REFERENCE TO RELATED APPLICATIONS

This application claims priority to U.S. provisional patent application 61/073,470 by Hathaway filed on Jun. 18, 2008 entitled "SPRING-TYPE SUTURE SECURING DEVICE," the entire contents of which are hereby incorporated by reference herein.

BACKGROUND

1. Technical Field

The present disclosure relates to endoscopic surgical devices and, more particularly, to endoscopic surgical graspers.

2. Background of Related Art

When performing endoluminal/transgastric surgery, it is necessary to tie a knot in the suture after the enterotomy (transgastric) or other defect is closed. Instruments are available to perform this function but are not user-friendly.

SUMMARY

To advance the state of the art with respect to efficiency of surgical procedures, the present disclosure relates to a suture securing device configured to engage an end portion of a suture prior to forming a knot.

More particularly, the present disclosure relates in one embodiment to a suture securing device includes a body having proximal and distal end portions. The distal end portion defines a suture receiving opening. The suture securing device also includes a shaft having proximal and distal end portions, the shaft at least partially disposed in the body, the shaft and the body being assembled for relative reciprocal motion between a first position and a second position. The suture securing device includes also a tension coil spring having a first end and a second end, the first end being operably attached to the distal end portion of the body and the second end being operably attached adjacent the distal end portion of the shaft, said tension coil spring disposed adjacent the suture receiving opening. The suture securing device is configured and dimensioned such that, when the body and shaft are in the first position, the tension coil spring is in a rest position, and when at least one of the body and the shaft are in the second position, the tension coil spring is in a tensioned position to form at least one gap therebetween to enable receipt of at least a portion of at least one suture.

In another embodiment, the present disclosure relates to a suture securing device that includes a body having proximal and distal end portions. The distal end portion defines a suture receiving opening. The suture securing device also includes a shaft having proximal and distal end portions, the shaft at least partially disposed in the body, the shaft and the body being assembled for relative reciprocal motion between a first position, a second position, and a third position. The suture securing device includes also a tension coil spring having a first end and a second end, the first end being operably attached to the distal end portion of the body and the second end being operably attached adjacent the distal end portion of the shaft, said tension coil spring disposed adjacent the suture receiving opening. The suture securing device is configured and dimensioned such that, when the body and shaft are in the first position, the tension coil spring is in a rest position, and when at least one of the body and the shaft are in the second position, the tension coil spring is in a tensioned position to form at least one gap therebetween to enable receipt of at least a portion of at least one suture.

In yet another embodiment, the present disclosure relates to a suture securing device that includes a body having proximal and distal end portions. The distal end portion defines a suture receiving opening. The suture securing device also includes a shaft having proximal and distal end portions, the shaft at least partially disposed in the body, the shaft being longitudinally movable relative to the body between a first position and a second position. The suture securing device includes also a tension coil spring having a first end and a second end, the first end being operably attached to the distal end portion of the body and the second end being operably attached adjacent the distal end portion of the shaft, said tension coil spring disposed adjacent the suture receiving opening. The suture securing device is configured and dimensioned such that, when the shaft is in the first position, the tension coil spring is in a rest position, and when the shaft is in the second position, the tension coil spring is in a tensioned position to form at least one gap therebetween to enable receipt of at least a portion of at least one suture.

In another embodiment, the present disclosure relates to a suture securing device that includes a body having proximal and distal end portions. The distal end portion defines a suture receiving opening. The suture securing device also includes a shaft having proximal and distal end portions, the shaft at least partially disposed in the body, the body being longitudinally movable relative to the distal end of the shaft between a first position and a second position. The suture securing device includes also a tension coil spring having a first end and a second end, the first end being operably attached to the distal end portion of the body and the second end being operably attached adjacent the distal end portion of the shaft, said tension coil spring disposed adjacent the suture receiving opening. The suture securing device is configured and dimensioned such that, when the body is in the first position, the tension coil spring is in a rest position, and when the body is in the second position, the tension coil spring is in a tensioned position to form at least one gap therebetween to enable receipt of at least a portion of at least one suture.

In still yet another embodiment, the present disclosure relates to a suture securing device that includes a body having proximal and distal end portions. The distal end portion defines a suture receiving opening. The suture securing device also includes a shaft having proximal and distal end portions, the shaft at least partially disposed in the body. The body is fixed relative to the distal end of the shaft. The body includes an extending member longitudinally movable relative to the body via the shaft between a first position and a second position. The suture securing device includes a tension coil spring having a first end and a second end, the first end being operably attached to the distal end portion of the body and the second end being operably attached adjacent the distal end portion of the shaft, the tension coil spring disposed adjacent the suture receiving opening. The suture securing device is configured and dimensioned such that, when the extending member is in the first position, the tension coil spring is in a rest position, and when the extending member is in the second position, the tension coil spring is in a tensioned position to form at least one gap therebetween to enable receipt of at least a portion of at least one suture.

DETAILED DESCRIPTION OF THE DRAWINGS

Various embodiments will be described herein below with reference to the drawings wherein:

FIG. 5A is a perspective view of a knuckle of the articulation joint of FIGS. 4A-4D;

FIG. 5B is a side view of the knuckle of the articulation joint of FIG. 5A;

FIG. 5C is an end view of the knuckle of the articulation joint of FIG. 5A;

FIG. 5D is a plan view of the knuckle of the articulation joint of FIG. 5A;

FIG. 8A is a side view of the handle assembly of FIG. 3A in a first orientation;

FIG. 8B is a side view of the handle assembly of FIG. 3A in a second orientation;

FIG. 8C is a perspective view of the handle assembly of FIG. 3A; and

FIG. 8D is an end view of the handle assembly of FIG. 3A.

DETAILED DESCRIPTION OF EXEMPLARY EMBODIMENTS

Figure 1:
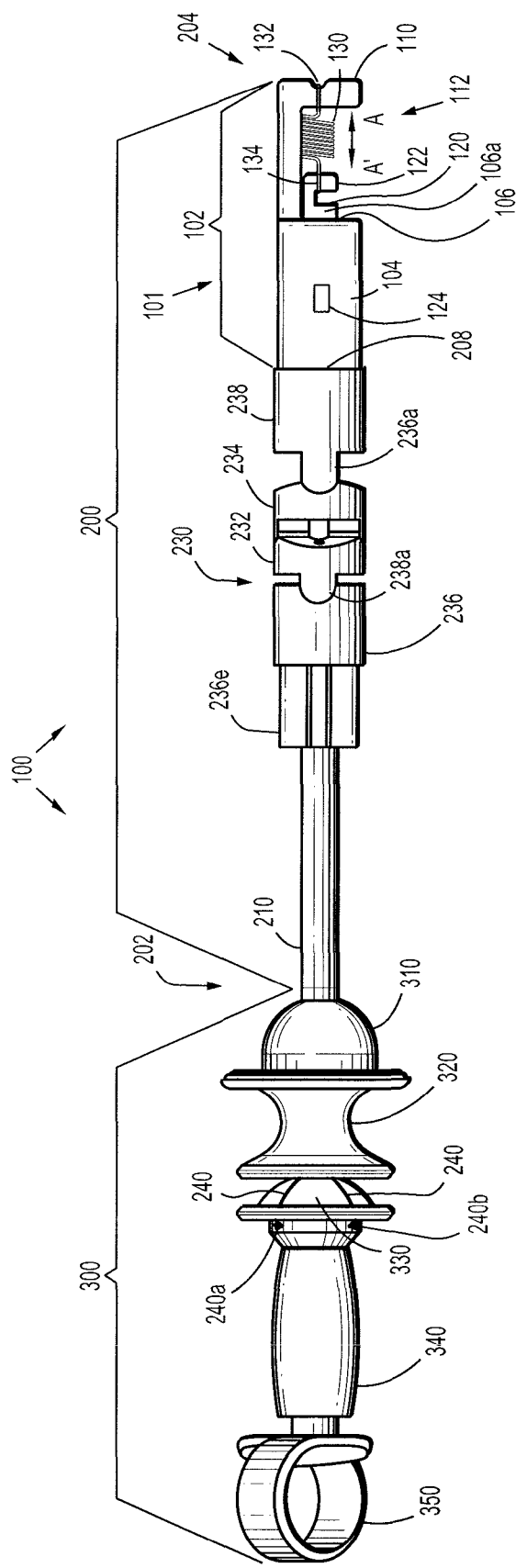
FIG. 1 is a view of an endoscopic surgical device having one embodiment of a suture securing device according to the present disclosure.

The present disclosure relates to an endoscopic surgical device that is configured with a suture securing device that enables securing of a suture in a user-friendly manner, thereby enabling simplified, less time-consuming surgical procedures to tie a suture knot and corresponding shorter procedure times and reduced surgeon workload.

When the suturing is completed and a knot is ready to be tied, the endoscopic surgical device is introduced into the lumen/area. The endoscopic surgical device, and particularly the suture securing device, is placed over the suture securely against the lumen/defect wall. The suture securing device includes a tension spring. The spring is allowed to re-compress so that the coils re-compress to capture the suture therebetween.

An alternative endoscopic surgical device having a related handle assembly is disclosed in commonly-owned U.S. patent application Ser. No. 12/193,864 by De Santis et al., filed on Aug. 19, 2008, entitled "ENDOSCOPIC SURGICAL DEVICE", the entire contents of which is hereby incorporated by reference herein.

Referring initially to FIGS. 1, 1A-1C and 2A-2C, an endoscopic surgical device configured to grasp or secure a suture is generally designated as 100. Surgical device 100 includes an endoscopic assembly 200 (see FIG. 2A-2C) operatively connected to and extending from a handle assembly 300 (see FIGS. 3A and 3B).

Endoscopic assembly 200 has a proximal end 202 and a distal end 204 and includes an outer tube 210 having a proximal end that coincides with proximal end 202 and that is secured to and that extends from handle assembly 300, an articulation assembly 230 supported on and extending from a distal end 206 of the outer tube 210, coinciding with a proximal end of the articulation assembly 230. The articulation assembly 230 extends to a distal end 208 thereof.

Endoscopic assembly 200 further includes an inner shaft 124, (e.g., a flexible cable or wire) that is slidably and rotatably supported within and extending through outer tube 210 and articulation assembly 230. A proximal end portion of the inner shaft 124 extends into handle assembly 300 and a distal end portion of the inner shaft 124 extends through the distal end 208 of the articulation assembly 230.

Figure 1A:
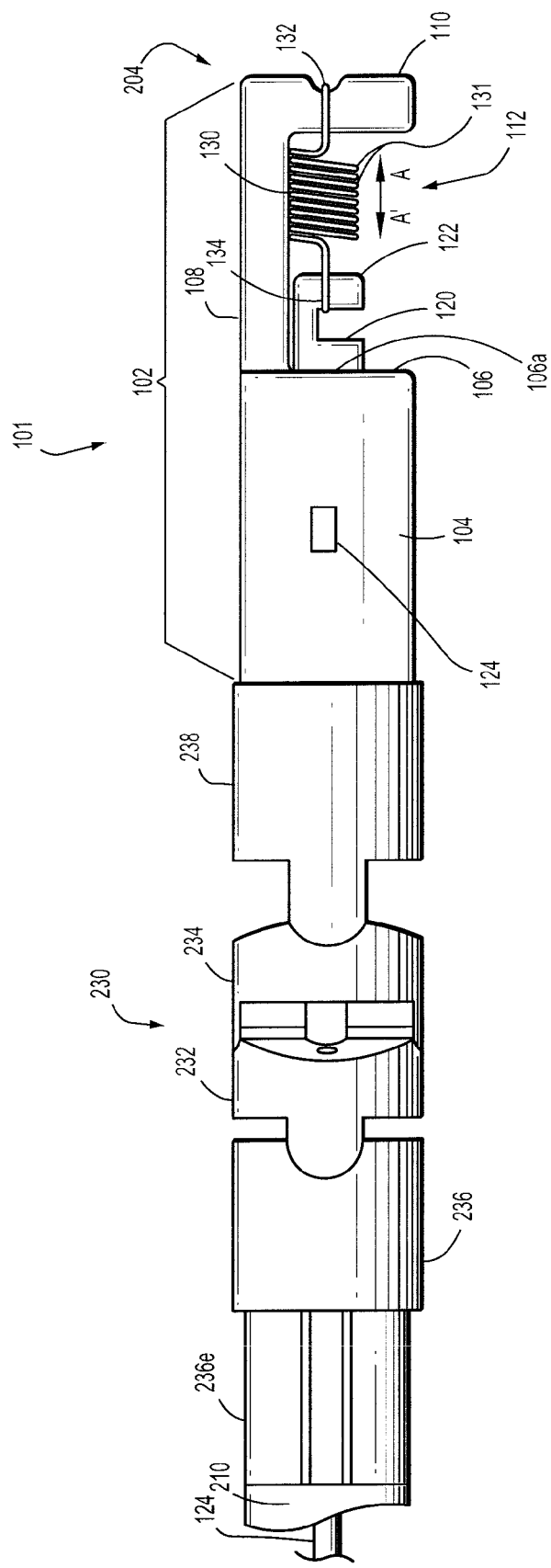
FIG. 1A is an enlarged view of one embodiment of a distal end of the endoscopic surgical device of FIG. 1 having a suture securing device according to the present disclosure.
Figure 1B:
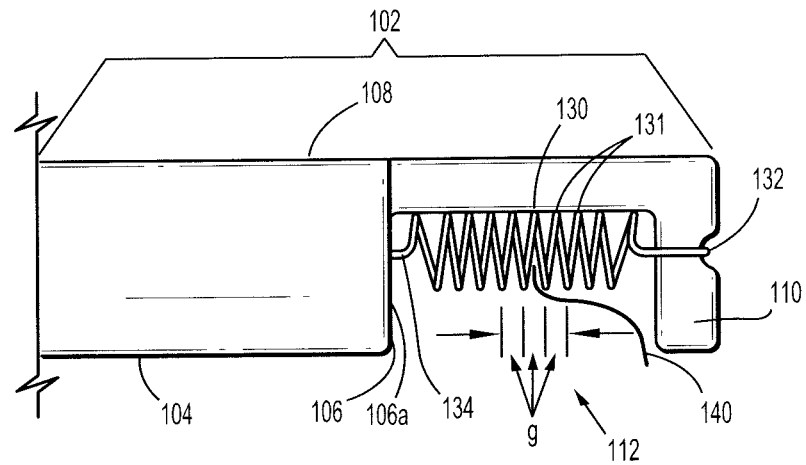
FIG. 1B is a partial view of the distal end of the suture securing device of FIG. 1A wherein the suture securing device is in an extended position to enable securing of a suture.
Figure 2A:
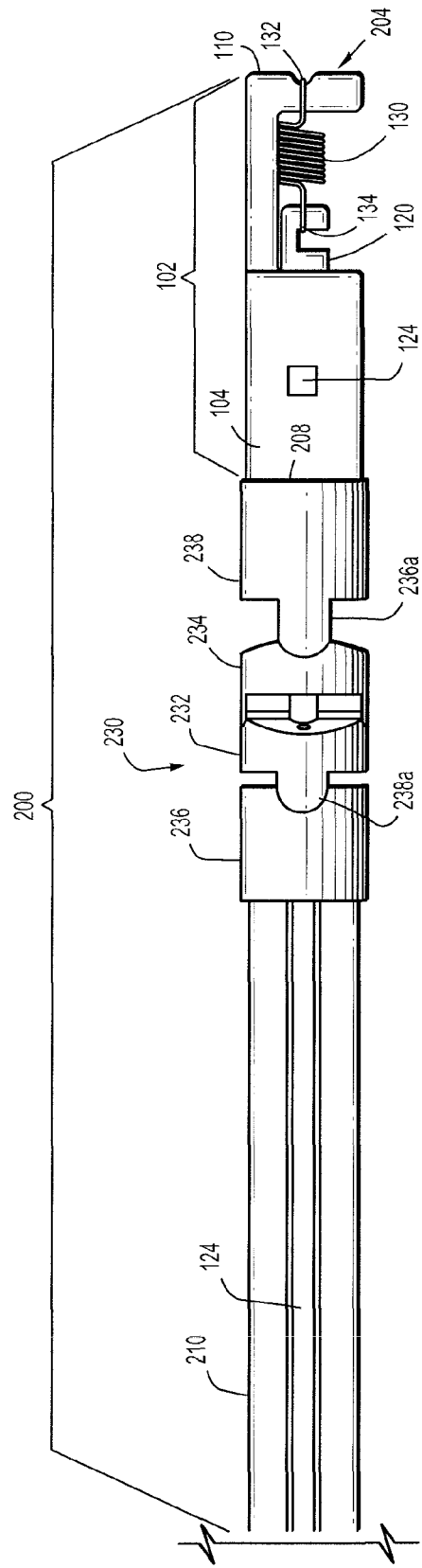
FIG. 2A is a view of the distal end of the suture securing device of FIG. 1A in a position offset from the baseline position.

Referring now to FIGS. 1A and 2A, the endoscopic assembly 200 includes a suture securing device 101 at the distal end 204. The suture securing device 101 includes a body 102 having a jaw or mounting member 104 and extends from a proximal end that may coincide with distal end 208 of the articulation assembly 230 and extends to a distal end that coincides with the distal end 204 of the endoscopic assembly 200 to define a suture receiving opening 112. The body 102 forms an internal volume 106, e.g., a cylindrically shaped tubular body with a hollow interior having a cylindrically shaped cross section, or a rectangularly shaped tubular body with a rectangularly shaped hollow interior or other suitable cross-sectional shape, that extends from distal end 208 of the articulation assembly 230 and that communicates with an open end 106a. As described above, the inner shaft 124 extends through the distal end 208 of the articulation assembly 230 and into the internal volume 106. The internal volume 106 formed by the body 102 is disposed to extend from the proximal end 208 to the open end 106a. The inner shaft 124 is at least partially disposed in the body 102, and the shaft 124 and the body 102 are assembled for relative reciprocal motion between at least a first position and a second position.

A support structure 108, which may be integrally formed as part of the mounting member 104, extends distally away from the open end 106a and towards the distal end 204 of the endoscopic assembly 200, to define the suture receiving opening 112 that is adjacent to the internal volume 106 at the open end 106a. The mounting member 104 may be configured with a lateral support bar 110 that may extend transversely from the support structure 108 to overhang and interface the open end 106a thereby.

A hook 120 is movably disposed within the internal volume 106 of the body 102 and has a retaining end 122. Additionally, a tension coil spring 130 has a first or distal end at which is disposed a first support interface structure 132 and a second or proximal end at which is disposed a second support interface structure 134, the support interface structures 132 and 134 being disposed adjacent the suture receiving opening 112. The first or distal and second or proximal support interface structures 132 and 134, respectively, may be configured as wire loops that are integrally formed with the spring 130.

In one embodiment, the spring 130 is configured to be supported at, or operably attached to, the first or distal support interface structure 132 by the support structure 108, and in particular by the lateral support bar 110. The spring 130 may be movably engaged with the retaining end 122 of the hook 120 at the second support interface structure 134. The proximal end of the hook 120 is operatively coupled to the inner shaft 124 that, as explained in more detail below, extends from the handle assembly 300 (See FIG. 3A). Relative reciprocal movement of the inner shaft 124 and correspondingly the hook 120, i.e., movement of the hook 120 from a first position at which the tension coil spring 130 is in a rest position, in a proximal direction generally along the centerline of the outer tube 210 in the direction indicated by arrow A' extends coils 131 of the coil spring 130 to a second or tensioned position to form at least one gap therebetween (see FIGS. 1A and 1B) to enable receipt of at least a portion of at least one suture 140 by the coil spring 130. That is, at least one gap g is formed between the coils 131 of the coil spring 130 that is sufficient to enable receipt of at least a portion of at least one suture 140 within the one or more gaps g.

Figure 1C:
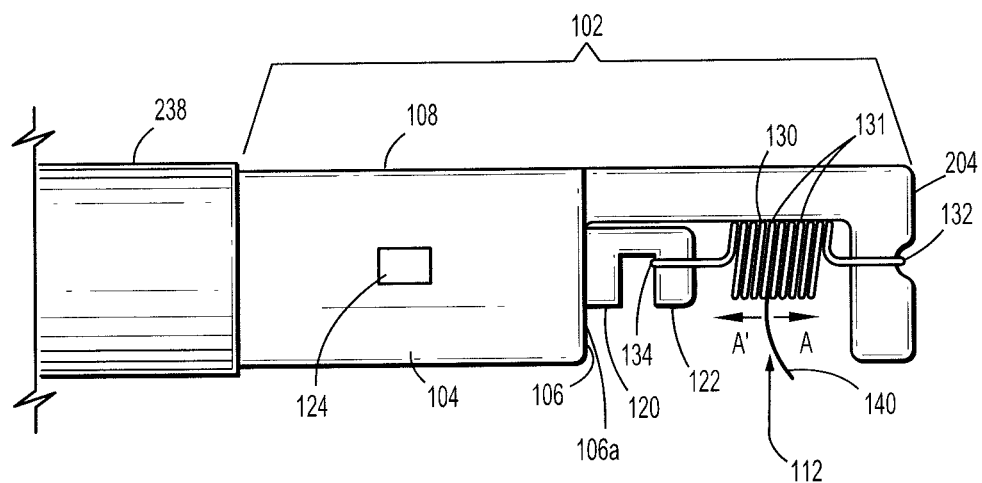
FIG. 1C is a partial view of the distal end of the suture securing device of FIG. 1A wherein the suture securing device is in a position at which securing of a suture occurs.

Referring to FIG. 1C, to perform the suture securing function, movement of the shaft 124 and correspondingly the hook 120 in the distal direction as indicated by arrow A enables the coils 131 of the coil spring 130, i.e., suture securing device 101, to transfer from the second or tensioned position to a third position by compressing the one or more gaps g to enable the coils 131 of the coil spring 130 to grasp or secure at least a portion of the one or more sutures 140 inserted therewithin. The first position of the coil spring 130 and the third position of the coil spring 130 are substantially identical except that in the third position, the coil spring position is slightly offset as compared to the first position by the securing of at least a portion of the one or more sutures 140 grasped between the coils 131.

Figure 1D:
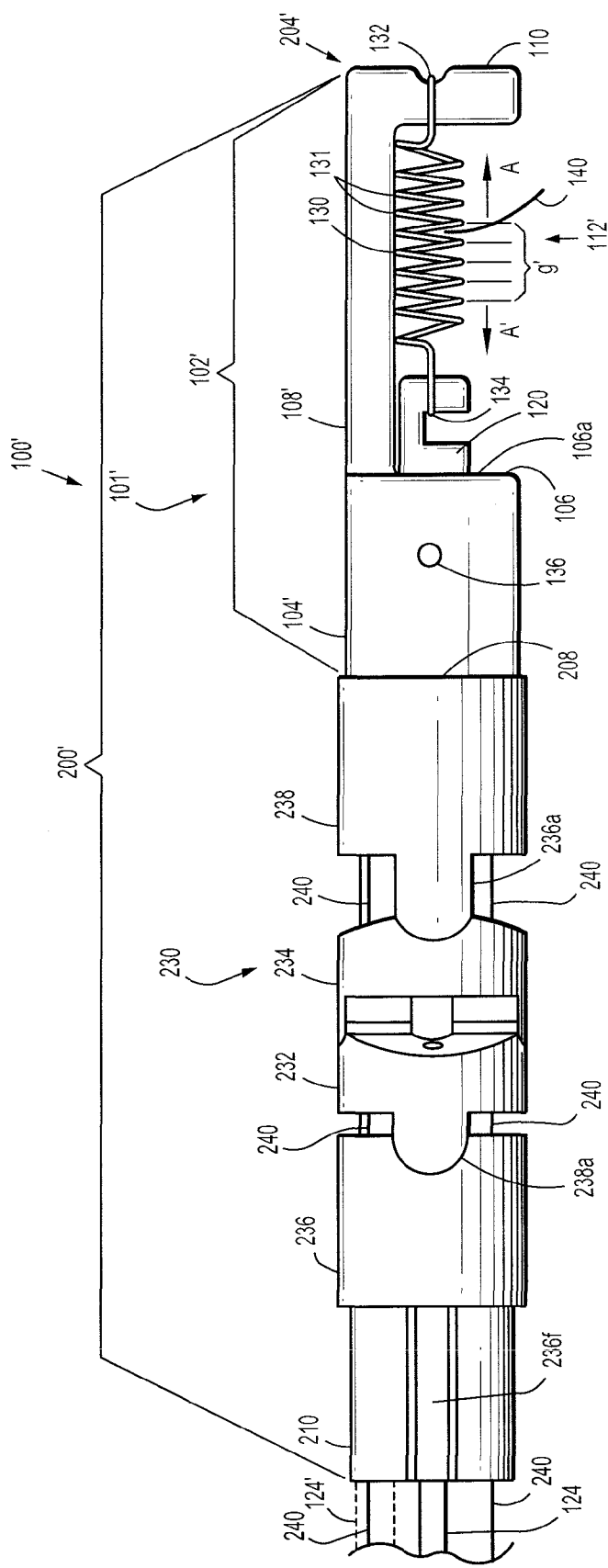
FIG. 1D is an enlarged view of an alternate embodiment of a distal end of a suture securing device according to the present disclosure.

FIG. 1D illustrates a partial view of another embodiment of an endoscopic surgical device with an endoscopic assembly having a suture securing device according to the present disclosure. More particularly, endoscopic surgical device 100' is identical to endoscopic surgical device 100 except that endoscopic assembly 200' includes a suture securing device 101' at the distal end 204 that, in turn, includes a body 102' having an extendable jaw or mounting member 104' that movably extends from a proximal end that may coincide with distal end 208 of the articulation assembly 230 and extends to a distal end that coincides with the distal end 204' of the endoscopic assembly 200' to define a suture receiving opening 112'. Consequently, endoscopic surgical device 100' will only be discussed in detail to the extent necessary to identify differences or similarities with respect to endoscopic surgical device 100.

In a manner similar to endoscopic surgical device 100, the body 102' forms an internal volume 106, e.g., a cylindrically shaped tubular body with a hollow interior having a cylindrically shaped cross section, or a rectangularly shaped tubular body with a rectangularly shaped hollow interior or other suitable cross-sectional shape, that extends from distal end 208 of the articulation assembly 230 and that communicates with open end 106a. In a similar manner, as described above, first or inner shaft 124 extends through the distal end 208 of the articulation assembly 230 and into the internal volume 106. The internal volume 106 formed by the body 102' is disposed to extend from the proximal end 208 to the open end 106a. The inner shaft 124 is at least partially disposed in the body 102', and the inner shaft 124 and the body 102' are assembled for relative reciprocal motion between at least a first position and a second position. However, suture securing device 101' differs from suture securing device 101 in that support structure 108' is now movably disposed as part of the body 102' to be capable of reciprocal motion towards and away from the proximal end 208 so that the extendable jaw or mounting member 104' is driven to cause relative reciprocal motion between at least a first position and a second position by a second shaft 124' that extends from the handle assembly 300 and which is operably coupled to the support structure 108' to cause the reciprocal motion thereof (see FIGS. 3A and 3B). Those skilled in the art will recognize how the articulation assembly 230, the outer tube 210 and the handle assembly 300 can be configured to accommodate the second shaft 124' to enable relative reciprocal motion of the extendable jaw or mounting member 104'.

Again, support structure 108' extends distally away from the open end 106a and towards the distal end 204' of the endoscopic assembly 200' to define the suture receiving opening 112' that is adjacent to the internal volume 106 at the open end 106a. The mounting member 104' may be configured with the lateral support bar 110 that may extend transversely from the support structure 108' to overhang and interface the open end 106a thereby.

In addition, the hook 120 may now be movably disposed within the internal volume 106 of the body 102' or alternatively, in view of the fact that the support structure 108' is capable of reciprocal motion to extend and retract the coil spring 130, the hook 120 may be fixedly attached to the body 102' by, for example, an attachment member 136, e.g., a bolt and nut combination or the like, so that the suture receiving opening 112' has a variable volume as the distal end 204' is extended and retracted.

As compared to endoscopic assembly 100, in the case when the hook 120 is not fixedly attached to the body 102' via the attachment member 136, relative reciprocal movement of the inner shaft 124 and correspondingly the hook 120, i.e., movement of the hook 120 from a first position at which the tension coil spring 130 is in a rest position, in a proximal direction generally along the centerline of the outer tube 210 in the direction indicated by arrow A', in combination with relative reciprocal motion of the second shaft 124' and correspondingly the support member 108', extends coils 131 of the coil spring 130 to a second or tensioned position to form at least one gap therebetween to enable receipt of at least a portion of at least one suture 140 by the coil spring 130. That is, at least one gap g' is formed between the coils 131 of the coil spring 130 that is sufficient to enable receipt of at least a portion of at least one suture 140 within the one or more gaps g'.

In contrast, when the hook 120 is fixedly attached to the body 102' by the attachment member 136, only the second shaft 124' and correspondingly the support member 108' are reciprocally movable to extend coil 131 of the coil spring 130 to a second or tensioned position to form at least one gap therebetween to enable receipt of at least a portion of at least one suture 140 by the coil spring 130, wherein, again, at least one gap g' is formed between the coils 131 of the coil spring 130 that is sufficient to enable receipt of at least a portion of at least one suture 140 within the one or more gaps g'.

To perform the suture securing function, movement of the first shaft 124 and/or the second shaft 124' and correspondingly the hook 120 in the distal direction as indicated by arrow A in the case of movement of the first shaft 124, and/or correspondingly the support member 108' in the proximal direction as indicated by arrow A', enables the coils 131 of the coil spring 130, i.e., suture securing device 130, to transfer from the second or tensioned position to a third position by compressing the one or more gaps g' to enable the coils 131 of the coil spring 130 to grasp or secure at least a portion of the one or more sutures 140 inserted therewithin. Again, the first position of the coil spring 130 and the third position of the coil spring 130 are substantially identical except that in the third position, the coil spring position is slightly offset as compared to the first position by the securing of at least a portion of the one or more sutures 140 grasped between the coils 131.

When the mounting member extends from the body as illustrated in FIG. 1D, and since the spring 130 may be rigidly attached to the body 102' via the hook 120 being fixedly attached to the body 102' by an attachment member 136, as previously described, those skilled in the art will recognize that, and understand how, at least one additional embodiment of the suture securing device 100', not shown explicitly in FIG. ID, may be configured wherein the spring 130 is extended by the second shaft 124' moving the extendable mounting member 108'. The first shaft 124 may be omitted entirely or decoupled from the hook 120. In the latter condition, the first shaft 124 may be included to provide stability to the endoscopic assembly 200 during articulation of the suture securing device 101.

Therefore, the body 102' is fixed relative to the distal end of the first shaft 124 or the second shaft 124' that each generally coincide with the distal end 208 of the articulation assembly 230. The body 102' includes the extending member, e.g., extendable jaw or mounting member 104', being longitudinally movable relative to the body 102' via the second shaft 124' between a first position and a second position.

The tension coil spring 130 again has the first end 132 being operably attached to the distal end portion 204' of the body 102' and the second end 134 being operably attached adjacent the distal end portion 208 of the second shaft 124', e.g., being operably attached to the hook 120 near the open end 106a of the internal volume 106. The tension coil spring 130 is again disposed adjacent the suture receiving opening 112', When the extending member 104' is in the first position, the tension coil spring 130 is in a rest position, and when the extending member 104' is in the second position, the tension coil spring 130 is in a tensioned position to form at least one gap g therebetween (see FIG. 1B) to enable receipt of at least a portion of at least one suture 140.

For all of the foregoing embodiments or variations thereof, the coil spring 130 is made from stainless steel, titanium or other material approved for biological use.

Figure 3A:
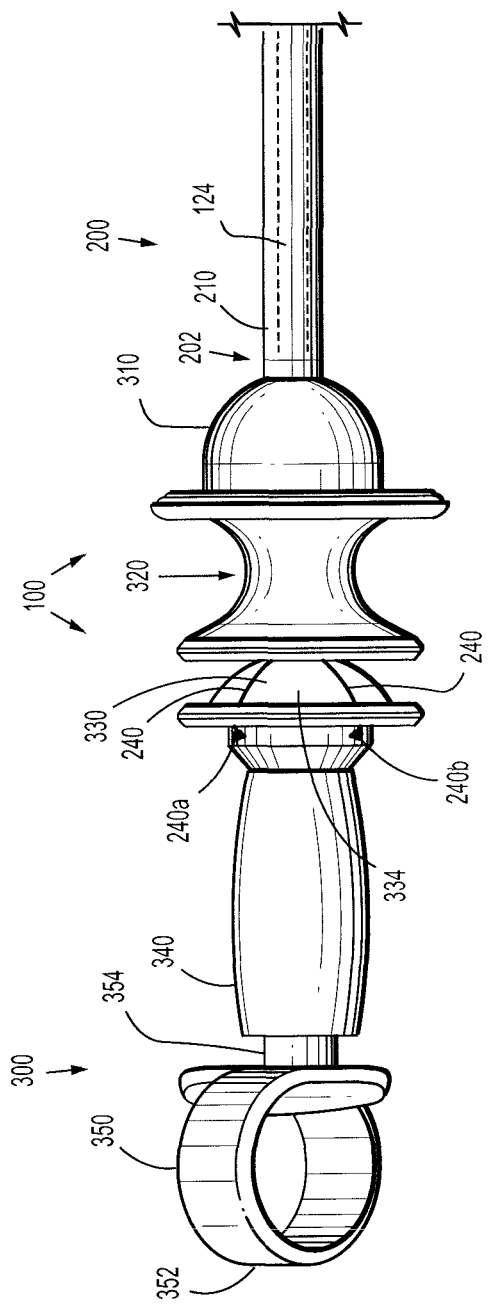
FIG. 3A is a perspective view of an exemplary handle assembly, shown in a straight or un-articulated position, configured to operate and articulate the embodiments of the suture securing device of the present disclosure.
Figure 3B:
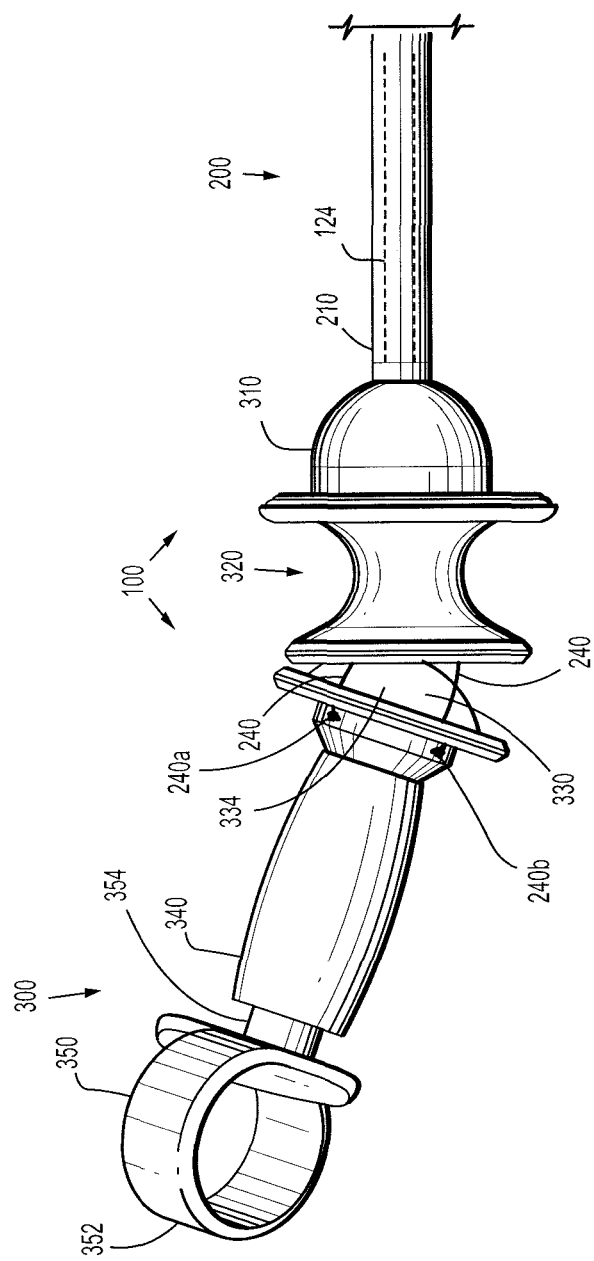
FIG. 3B is a perspective view of the exemplary handle assembly of FIG. 3A, shown in a canted or articulated position.
Figure 4A:
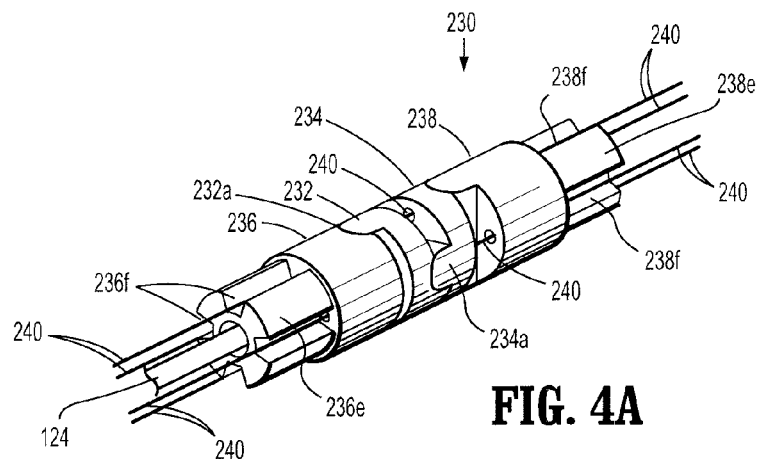
FIG. 4A is a perspective view of an articulation joint of the suture securing device of FIG. 1A.
Figure 4B:
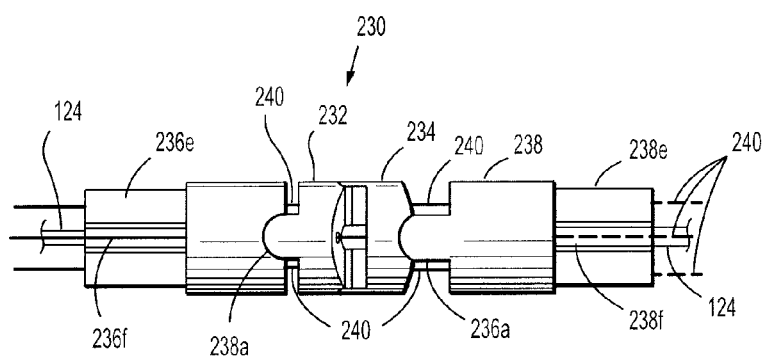
FIG. 4B is a top view of the articulation joint of FIG. 4A.
Figures 4C, 4D:
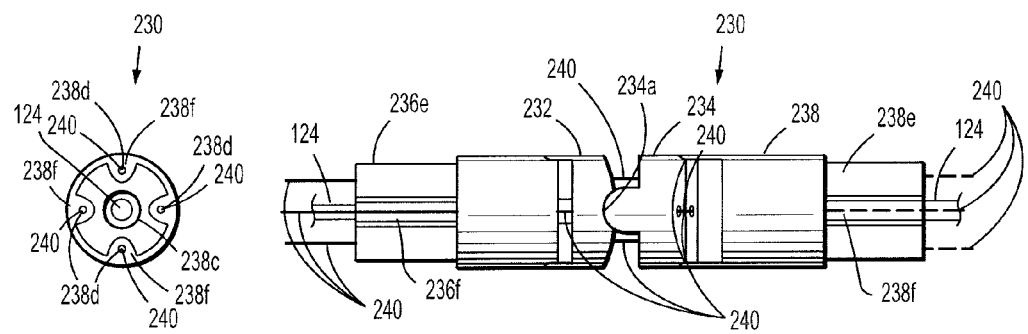
FIG. 4C is a side view of the articulation joint of FIG. 4A.
FIG. 4D is a cross-sectional end view of the articulation joint of FIG. 4A.
Figure 6A:
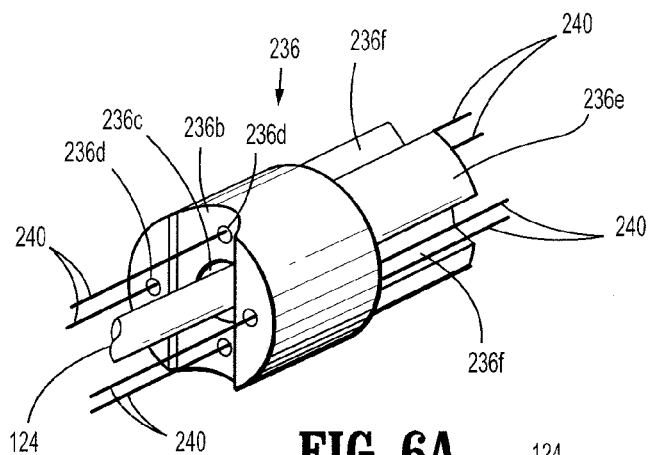
FIG. 6A is a perspective view of a first connector of the articulation joint of FIGS. 4A-4D.
Figure 6B:
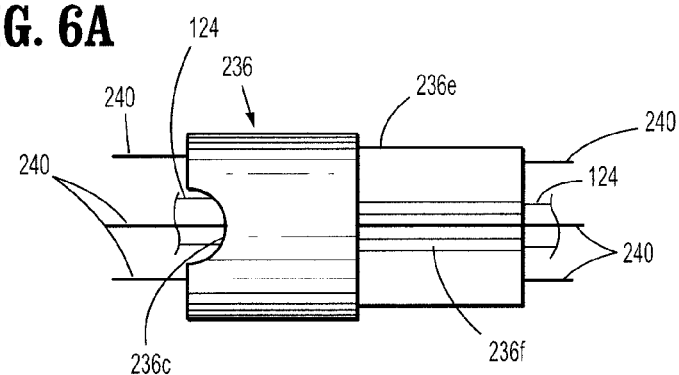
FIG. 6B is a plan view of the first connector of the articulation joint of FIG. 6A.
Figure 6D:
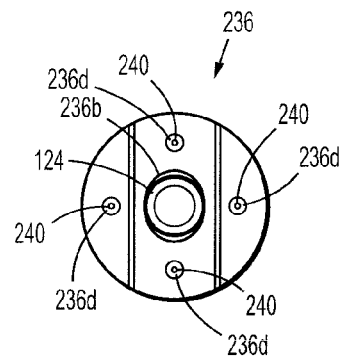
FIG. 6D is an end view of the first connector of the articulation joint of FIG. 6A.
Figure 6C:
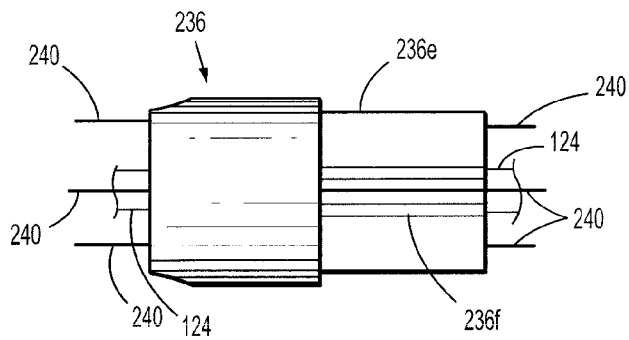
FIG. 6C is a side view of the first connector of the articulation joint of FIG. 6A.
Figure 7A:
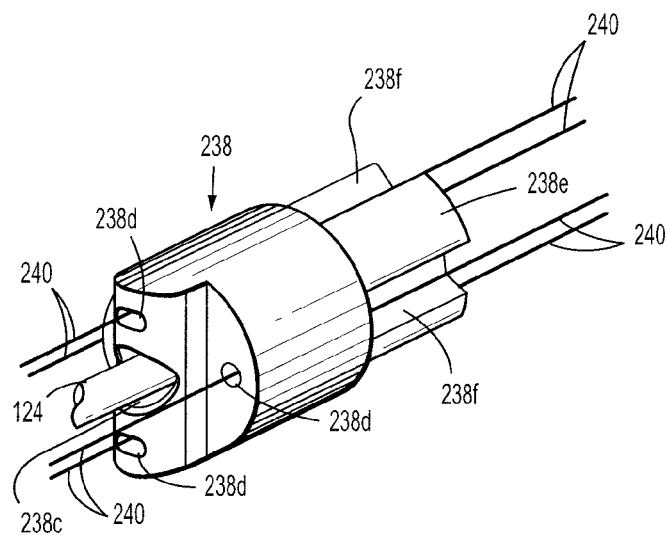
FIG. 7A is a perspective view of a first connector of the articulation joint of FIGS. 4A-4D.
Figure 7B:
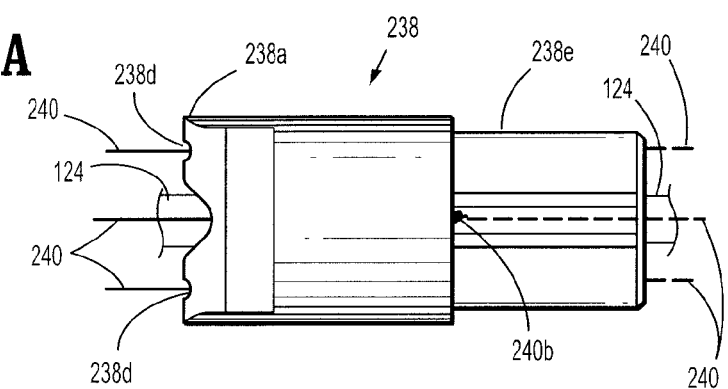
FIG. 7B is a side view of the first connector of the articulation joint of FIG. 7A.
Figure 7D:
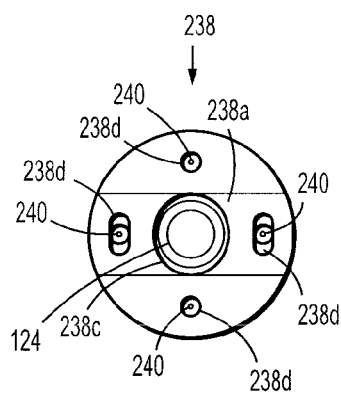
FIG. 7D is an end view of the first connector of the articulation joint of FIG. 7A.
Figure 7C:
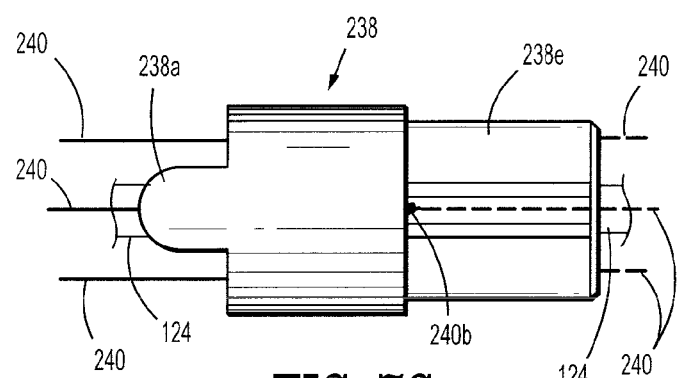
FIG. 7C is an end view of the first connector of the articulation joint of FIG. 7A.

The endoscopic assembly 200 (or 200'), and consequently the suture securing device 101 (or 101'), is configured to be operated and articulated by various types of handle assemblies such as exemplified by the handle assembly 300. In general, as seen in FIGS. 3A and 3B, the handle assembly 300 may be configured so as to be held in a hand of an operator in the manner of a syringe or the like and is configured to be operated, if desired, solely with said hand.

As seen in FIGS. 1, 2A-2C and 4A-7D, articulation assembly 230 includes at least a pair of joints 232, 234 configured for pivotable movement relative to one another. Each joint 232, 234 includes a respective knuckle 232a, 234a and a respective clevis 232b, 234b formed therewith. Each knuckle operatively engages a clevis of an adjacent joint so as to define a pivot axis. Each joint 232, 234 defines a respective central lumen 232c, 234c formed therethrough for receipt of the inner shaft 124 therein and two-pair of diametrically opposed lumens 232d, 234d formed around central lumen 232c, 234c. Articulation cables 240 are provided and slidably extend through lumens 232d, 234d of joints 232, 234.

Articulation assembly 230 includes a proximal support joint 236 supported at the distal end of proximal outer tube 210 and defining a clevis 236b configured to pivotably engage a knuckle of joints 232, 234, and a distal support joint 238 supported at a proximal end of distal outer tube 220 and defining a knuckle 238a configured to pivotably engage a clevis of joints 232, 234. Each support joint 236, 238 includes two-pair of diametrically opposed lumens 236d, 238d formed around a central lumen 236c, 238c thereof. Each support joint 236, 238 further includes a generally cylindrically-shaped stem 236e, 238e for receipt in outer tube 210. The articulation cables 240 that slidably extend through lumens 232d, 234d also slidably extend through the lumens 236d, 238d. The central lumen 236c, 238c formed in the support joints 236, 238 also is formed in and extends through the central portion of the cylindrically-shaped stems 236e, 238e to establish an inner periphery therein. The stems 236e, 238e each include two-pair of diametrically opposed open channels 236f, 238f on the outer periphery thereof. The articulation cables 240 that slidably extend through lumens 232d, 234d and 236d, 238d also further slidably extend through the open channels 236f, 238f. In the case of a single articulation assembly 230, the articulation cables 240 may be anchored at anchor points 240b at the proximal end of the stem 238e. In the case of multiple articulation assemblies 230, the articulation cables 240, shown dotted, may further slidably extend through the open channels 238f of stem 238e.

Figure 2B:
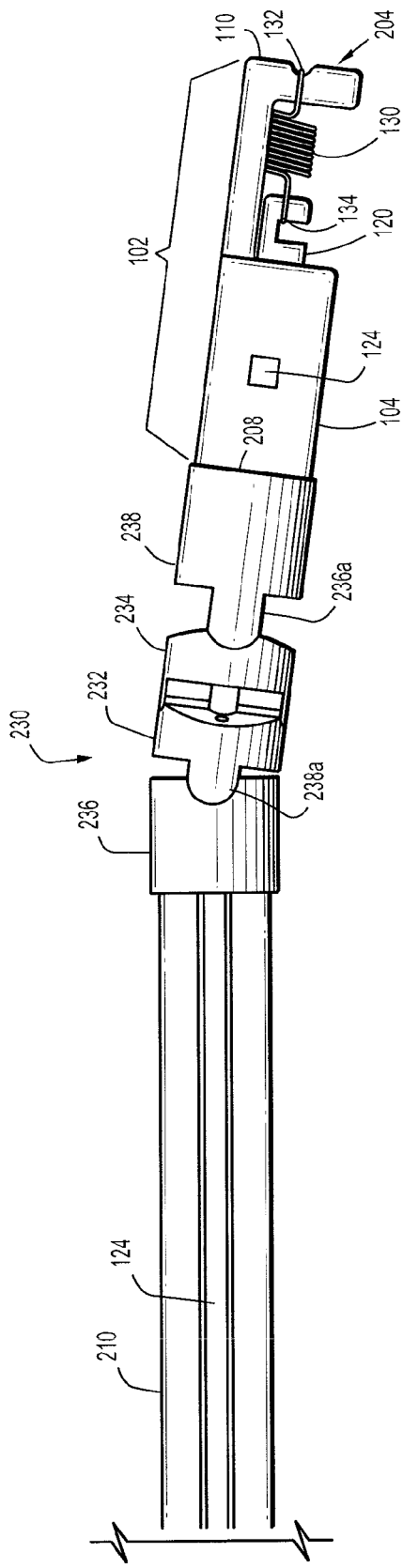
FIG. 2B is a view of the distal end of the suture securing device of FIG. 1A in one angle of articulation with respect to the baseline position.
Figure 2C:
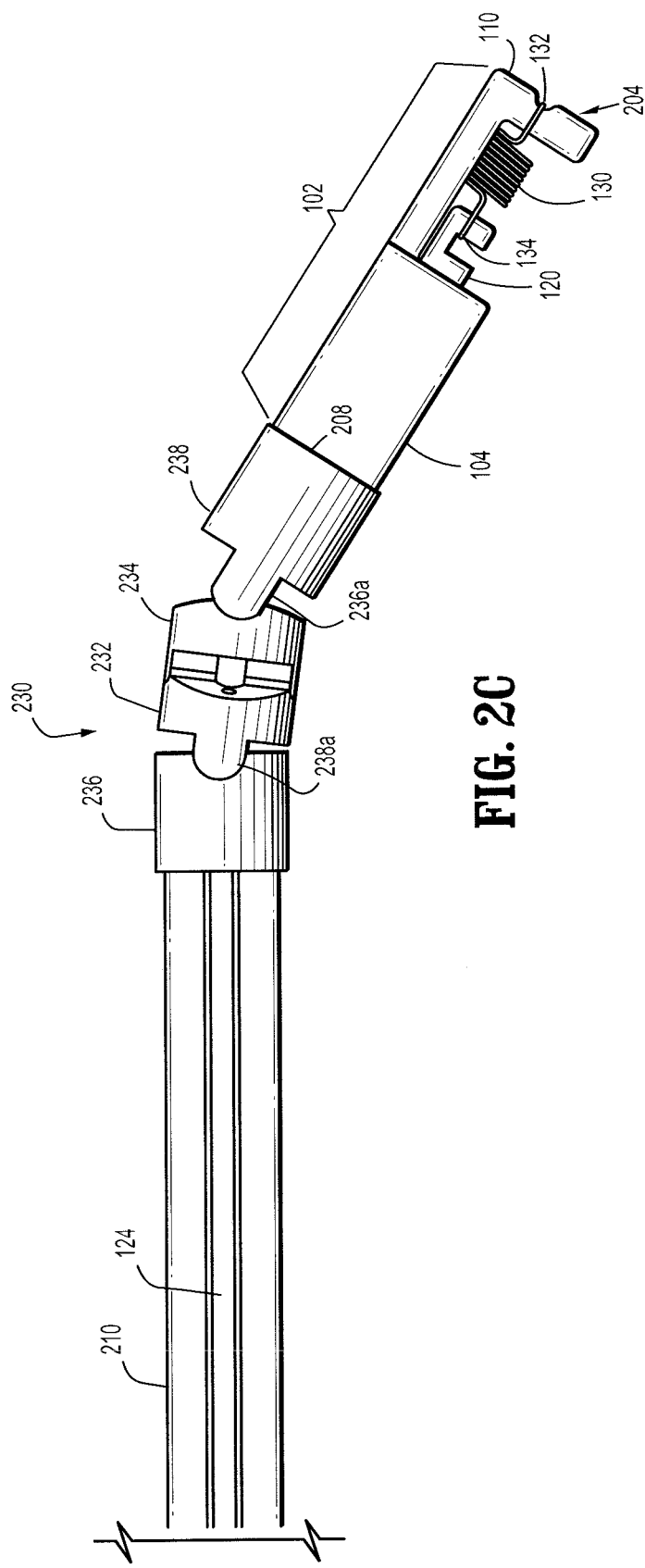
FIG. 2C is a view of the distal end of the suture securing device of FIG. 1A in another angle of articulation with respect to the baseline position.

The articulation cables 240, thus extending through the knuckles and clevis pair of the joints 232, 234, and being slidably extended therethrough enable the knuckles and clevis pair to be alternatingly oriented orthogonal to an adjacent knuckle/clevis pair by movement of the articulation cables 240 so as to enable articulation joint 230 to articulate in at least two degrees, i.e., in the plane of the page as seen in FIGS. 2B and 2C, and out of the plane of the page (not shown) to provide articulation of the suture securing device 101 (or 101') at the distal end 204. It is contemplated that any number of joints 232, 234 may be provided as needed or desired. It is understood that the greater the number of joints provided the greater the degree of articulation of the distal end 204 of endoscopic device 100 and correspondingly the greater the degree of articulation of the suture securing device 101 (or 101').

As seen in FIGS. 3A, 3B and 8A-8D, there is illustrated an exemplary embodiment of a handle assembly that is suitable to operate the endoscopic assembly 200 (or 200'), and particularly the suture securing device 101 (or 101'), of the present disclosure. More particularly, handle assembly 300 includes a hub 310 operatively connected to proximal end 202 of outer tube 210, a spool 320 operatively supported on and/or connected to hub 310, a ball joint 330 operatively supported on and/or connected to spool 320, a collar 340 operatively supported on and/or connected to ball joint 330; and an actuator 350 operatively supported in and through collar 340.

As seen in FIGS. 3A, 3B and 8A-8D, spool 320 defines a concave outer annular side-wall profile 320a and a central lumen (not shown) extending through said spool. The concavity of the profile of the side-wall may be such as to accommodate a digit of the hand of the user, such as for example the middle and ring fingers on either side thereof. Spool 320 is free to rotate relative to hub 310. A detailed description of the handle assembly 300 is provided in above-referenced U.S. patent application Ser. No. 12/193,864 by De Santis et al.

As seen in FIGS. 8A and 8B, a proximal surface 320' of spool 320 may have a concave profile. Additionally, as seen in 8C, spool 320 includes two-pair of diametrically opposed lumens 326 (only partially shown) formed around the central lumen (not shown) and extending entirely through spool 320. Lumens 326 are configured to slidably receive articulation cables 240 therein.

As seen in FIGS. 3A, 3B and 8A-8C, ball joint 330 may be formed in a pair of halves 332a, 332b which are joined or mated to one another define a central lumen (not shown) therethrough. Ball joint 330 defines an arcuate distal surface 334 having a convex profile configured for operative engagement with the concave proximal surface of spool 320.

Referring to FIGS. 1, 2A-2C, 3A-3B, and 4A-8D, endoscopic device 100 includes a plurality of the articulation cables 240 each having a first end 240a anchored to flange 336 of ball joint 330 and a second end 240b extending through respective lumens 326 formed in spool 320, into lumen 316 of hub 310, through proximal outer tube 210, through respective lumens 232d, 234d formed in joints 232, 234, and anchored at anchor points 240b to distal support joint 238 of articulation assembly 230, as explained above. In operation, as ball joint 330 is pivoted relative to spool 320, articulation cables 240, being generally flexible but sufficiently rigid to maintain a generally linear configuration without substantial buckling when in compression due to pushing, are either pulled or pushed to effectuate articulation of the distal end 204 of endoscopic assembly 200 (or 200'), and specifically the suture securing device 101 (or 101'), via articulation of the articulation assembly 230 (see FIGS. 1 and 2A-2C).

As seen in FIGS. 3A, 3B and 8A-8D, collar 340 may be formed in a pair of halves 342a, 342b which are joined or mated to one another define a lumen or cavity 342c (see FIG. 8C) therethrough. Collar 340 is free to rotate relative to ball joint 330 without causing rotation or twisting of the articulation cables 240.

As seen in FIGS. 3A, 3B, actuator 350 may include a loop 352 and a stem 354 extending therefrom. Loop 352 may be configured and dimensioned to receive a digit of the hand of the operator therein, such as, for example, the thumb. Actuator 350 is supported on a proximal end of collar 340 such that stem 354 extends into lumen 342c thereof.

In operation, with reference to FIGS. 1, 2A-3B and 8A-8D, as actuator 350 is translated relative to collar 340, as indicated by double-headed arrow A (see FIGS. 8A-8C), socket joint 356 transmits said translation to the inner shaft 124 which in turn transmits said translation to the hook 120 supported at the distal end thereof, to effectuate extension and retraction of suture securing device 101 (or 101') via movement of the hook 120.

It is contemplated that handle assembly 300 may be provided with a locking or ratchet mechanism configured and adapted to function to maintain the position of actuator 350 as actuator 350 is depressed in a distal direction or towards hub 310. In this manner, suture securing device 101 (or 101') may be held in a fixed position, either fully open, partially open or completely closed. (Fully open is defined herein as the average size of the gaps g or g' (see FIGS. 1A and 1C) achievable during operation of the endoscopic surgical device 100 (or 100') by an average user and is a function at least of the material and spring constant of the spring 130). It is further contemplated that the locking or ratchet mechanism will disengage, thereby allowing actuator 350 to return to an un-depressed position, following complete depression of actuator 350. It is also contemplated that actuator 350 may be biased to the un-depressed position by a suitable biasing element, such as, for example, a compression spring or the like.

Additionally, in operation, as collar 340 is rotated about the longitudinal axis, as indicated by arrows B, relative to ball joint 330, spool 320 and actuator 350, collar 340 transmits rotation to a key member (not shown), the key member imparts axial rotation to the inner shaft 124. As the inner shaft is rotated along the longitudinal axis D, the inner shaft 124 imparts rotation to the endoscopic assembly 200 (or 200') and particularly suture securing device 101 (or 101'), as indicated by arrows B of FIG. 8D.

It is contemplated that handle assembly 300 may be provided with a locking or ratchet mechanism configured and adapted to function to maintain the position of collar 340 as collar 340 is rotated relative to ball joint 330, spool 320 and/or hub 310. In this manner, the angular orientation of endoscopic assembly 200 (or 200') may be held in a fixed position. It is further contemplated that the locking or ratchet mechanism may be disengaged, thereby allowing collar 340 to freely rotate once again.

Also, in operation, as ball joint 330 is pivoted at the interface between arcuate distal surface 334 thereof and concave proximal surface of spool 320, in any radial direction relative to the longitudinal axis, as exemplarily indicated by arrows C, articulation cables 240 are pulled and/or pushed to effectuate articulation of the distal en 204 of endoscopic assembly 200 (or 200') in any radial direction relative to the longitudinal axis.

It is contemplated that, alternatively or additionally, handle assembly 300 may be provided with a locking or ratchet mechanism configured and adapted to function to maintain the position of ball joint 330 as ball joint 330 is pivoted off-axis relative to spool 320 and/or hub 310. In this manner, the articulation of endoscopic assembly 200 (or 200') and particularly body 102 (or 102') and suture securing device 101 (or 101') may be held in a fixed position. It is further contemplated that the locking or ratchet mechanism may be disengaged, thereby allowing ball joint 330 to return to a centered position and endoscopic assembly 200 and particularly body 102 (or 102') and suture securing device 101 (or 101') returned to a non-articulated position.

While several embodiments of the disclosure have been shown in the drawings, it is not intended that the disclosure be limited thereto, as it is intended that the disclosures be as broad in scope as the art will allow and that the specification be read likewise. Therefore, the above description should not be construed as limiting, but merely as exemplifications of particular embodiments.

What is claimed is:

1. A suture securing device comprising:
   a body having proximal and distal end portions, the distal end portion defining a suture receiving opening;
   a shaft having proximal and distal end portions, the shaft at least partially disposed in the body, the shaft and the body being assembled for relative reciprocal longitudinal motion between a first position and a second position;
   a tension coil spring having a first end and a second end, the first end being operably attached to the distal end portion of the body and the second end being operably attached adjacent the distal end portion of the shaft, said tension coil spring disposed adjacent the suture receiving opening, said tension coil spring assembled for relative reciprocal longitudinal motion; and
   a mounting member attached to the body, the first end of the tension coil spring being operably attached to the distal end portion of the body via the mounting member, the second end of the tension coil spring being operably attached to the distal end portion of the shaft via the mounting member,
   wherein the suture securing device is configured and dimensioned such that, when said body and shaft are in the first position, the tension coil spring is in a rest position, and when at least one of the body and the shaft are in the second position, the tension coil spring is in a tensioned position at a point along a path defined by the relative reciprocal longitudinal motion of the tension coil spring to form at least one gap therebetween to enable receipt of at least a portion of at least one suture and
   wherein relative reciprocal motion of the shaft with respect to the body effects the relative reciprocal motion between the first position and the second position.

2. The suture securing device according to claim 1, wherein the shaft and the body are assembled for relative reciprocal longitudinal motion between the first position, the second position and a third position.

3. The suture securing device according to claim 2, wherein the suture securing device is configured and dimensioned such that when the body and shaft are in the third position, the tension coil spring is in a position to enable securing of at least a portion of at least one suture by the tension coil spring.

4. The suture securing device according to claim 1, wherein the suture securing device is configured and dimensioned such that movement of at least one of the body and the shaft enables the coils of the coil spring to compress the at least one gap to enable the coils of the coil spring to grasp the at least a portion of at least one suture inserted within the at least one gap.

5. A suture securing device comprising:
   a body having proximal and distal end portions, the distal end portion defining a suture receiving opening;
   a shaft having proximal and distal end portions, the shaft at least partially disposed in the body, the shaft and the body being assembled for relative reciprocal longitudinal motion between a first position, a second position, and a third position;
   a tension coil spring having a first end and a second end, the first end being operably attached to the distal end portion of the body and the second end being operably attached adjacent the distal end portion of the shaft, said tension coil spring disposed adjacent the suture receiving opening, said tension coil spring assembled for relative reciprocal longitudinal motion; and
   a mounting member attached to the body, the first end of the tension coil spring being operably attached to the distal end portion of the body via the mounting member, the second end of the tension coil spring being operably attached to the distal end portion of the shaft via the mounting member,
   wherein the suture securing device is configured and dimensioned such that, when said body and shaft are in the first position, the tension coil spring is in a rest position, and when at least one of the body and the shaft are in the second position, the tension coil spring is in a tensioned position at a point along a path defined by the relative reciprocal longitudinal motion of the tension coil spring to form at least one gap therebetween to enable receipt of at least a portion of at least one suture and
   wherein relative reciprocal motion of the shaft or the body effects the relative reciprocal motion between the first position and the second position.

6. The suture securing device according to claim 5, wherein the suture securing device is configured and dimensioned such that when the body and shaft are in the third position, the tension coil spring is in a position to enable securing of at least a portion of at least one suture by the tension coil spring.

7. The suture securing device according to claim 6, wherein the suture securing device is configured and dimensioned such that movement of at least one of the body and the shaft extends the coils of the coil spring to form at least one gap therebetween that is sufficient to enable at least a portion of at least one suture to be inserted within the at least one gap.

8. The suture securing device according to claim 6, wherein the suture securing device is configured and dimensioned such that movement of at least one of the body and the shaft enables the coils of the coil spring to compress the at least one gap to enable the coils of the coil spring to grasp the at least a portion of at least one suture inserted within the at least one gap.

9. A suture securing device comprising:
   a body having proximal and distal end portions, the distal end portion defining a suture receiving opening;
   a shaft having proximal and distal end portions, the shaft at least partially disposed in the body, the shaft being longitudinally movable relative to the body between a first position and a second position; and
   a tension coil spring having a first end and a second end, the first end being operably attached to the distal end portion of the body and the second end being operably attached adjacent the distal end portion of the shaft, said tension coil spring disposed adjacent the suture receiving opening, said tension coil spring assembled for relative reciprocal longitudinal motion; and
   a mounting member attached to the body, the first end of the tension coil spring being operably attached to the distal end portion of the body via the mounting member, the second end of the tension coil spring being operably attached to the distal end portion of the shaft via the mounting member,
   wherein the suture securing device is configured and dimensioned such that, when said shaft is in the first position, the tension coil spring is in a rest position, and when the shaft is in the second position, the tension coil spring is in a tensioned position at a point along a path defined by the relative reciprocal longitudinal motion of the tension coil spring to form at least one gap therebetween to enable receipt of at least a portion of at least one suture and wherein relative reciprocal longitudinal motion of the shaft with respect to the body effects longitudinal movement of the shaft relative to the body between the first position and the second position.

10. The suture securing device according to claim 9, wherein the shaft and the body are assembled for relative longitudinal reciprocal motion between the first position, the second position and a third position.

11. The suture securing device according to claim 10, wherein the suture securing device is configured and dimensioned such that when the body and shaft are in the third position, the tension coil spring is in a position to enable securing of at least a portion of at least one suture by the tension coil spring.

12. A suture securing device comprising:
a body having proximal and distal end portions, the distal end portion defining a suture receiving opening;
a shaft having proximal and distal end portions, the shaft at least partially disposed in the body, the body being longitudinally movable relative to the distal end of the shaft between a first position and a second position; and
a tension coil spring having a first end and a second end, the first end being operably attached to the distal end portion of the body and the second end being operably attached adjacent the distal end portion of the shaft, said tension coil spring disposed adjacent the suture receiving opening, said tension coil spring assembled for relative reciprocal longitudinal motion; and
a mounting member that is fixedly attached to the body, the first end of the tension coil spring being operably attached to the distal end portion of the body via the mounting member, the second end of the tension coil spring being operably attached to the distal end portion of the shaft via the mounting member,
wherein the suture securing device is configured and dimensioned such that, when said body is in the first position, the tension coil spring is in a rest position, and when the body is in the second position, the tension coil spring is in a tensioned position at a point along a path defined by the relative reciprocal longitudinal motion of the tension coil spring to form at least one gap therebetween to enable receipt of at least a portion of at least one suture, and
wherein longitudinal movement of the body relative to the distal end of the shaft effects longitudinal movement of the body relative to the distal end of the shaft between the first position and the second position.

* * * * *